United States Patent [19]
Bedeschi et al.

[11] Patent Number: 5,360,904
[45] Date of Patent: Nov. 1, 1994

[54] PROCESS FOR PREPARING PENEM ESTERS

[75] Inventors: Angelo Bedeschi; Walter Cabri, both of Milan; Marcello Marchi, Novara; Ettore Perrone, Boffalora Ticino, all of Italy

[73] Assignee: Farmitalia Carlo Erba S r l, Milan, Italy

[21] Appl. No.: 927,511

[22] PCT Filed: Mar. 18, 1991

[86] PCT No.: PCT/EP91/00522

§ 371 Date: Sep. 21, 1992

§ 102(e) Date: Sep. 21, 1992

[87] PCT Pub. No.: WO91/14691

PCT Pub. Date: Oct. 3, 1991

[30] Foreign Application Priority Data

Mar. 19, 1990 [GB] United Kingdom ............... 9006114.4

[51] Int. Cl.$^5$ .......................................... C07D 499/00
[52] U.S. Cl. ........................................ 540/310; 540/350
[58] Field of Search ................. 540/310, 350; 514/210

[56] References Cited

U.S. PATENT DOCUMENTS 5,153,315 10/1992 Hungerbühler et al. ............ 540/310

FOREIGN PATENT DOCUMENTS 0215739 3/1987 European Pat. Off. .
0406790 1/1991 European Pat. Off. .
2097786 11/1982 United Kingdom .

OTHER PUBLICATIONS

Tetrahedron Letters, vol. 34, No. 21, pp. 3491–3492, "The Total Synthesis of Ritipenems. Construction of Penem Thiazoline Ring by Incorporation of Two 2C Units of Glycolic Acid", Walter Cabri, et al. (Mar. 26, 1993).

Primary Examiner—Nicholas Rizzo
Attorney, Agent, or Firm—Oblon, Spivak, McClelland, Maier & Neustadt

[57] ABSTRACT

A process for preparing penem esters by reacting

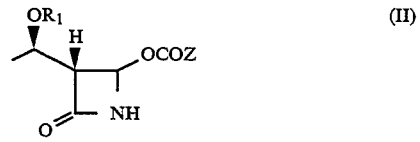

(II)

wherein $R_1$ is a hydroxy protecting group and X is a $C_1$-$C_{10}$ alkyl or aryl group, with

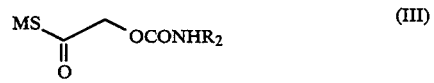

(III)

wherein $R_2$ is hydrogen or a $C_1$-$C_6$ alkyl group in the presence of an anhydrous organic solvent, condensing the product with

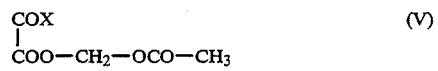

(V)

wherein X is a halogen atom or a —OCOOR$_3$ group and then cyclizing.

17 Claims, No Drawings

PROCESS FOR PREPARING PENEM ESTERS

The present invention relates to a novel process for preparing penem esters starting from a suitable oxalic acid derivative and an appropriate azetidinone.

It is known that the penems are useful as antibacterial agents as described and claimed in e.g. U.S. Pat. No. 4,482,565.

The penems may be prepared by means of many processes as for example those shown in GB-A-2144743 or in GB A-2111496. The known methods of preparation require long syntheses and the use of expensive protecting groups and reagents; for example, the preparation of the intermediate acetoxymethyl oxalic acid requires a multistep synthesis starting from an expensive oxalyl chloride; moreover the preparation of the azetidinones is characterized by low yields and poor purity of the desired intermediates.

We have found a new method to obtain penem esters under very mild conditions, with high stereoselectively, high yields and an easy workup and a new method for the preparation of acetoxymethyl oxalic acid starting from an unexpensive reagent with an easy procedure.

According to the present invention, there is provided a process for preparing a compound of the formula (I):

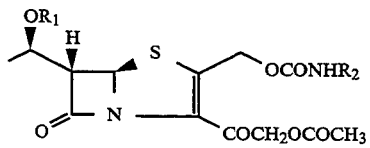

wherein $R_1$ is a hydrogen atom or a hydroxy protecting group and $R_2$ is a hydrogen atom or a $C_1$-$C_6$ alkyl group, the process comprising the following steps:

a) reacting a compound of the formula (II)

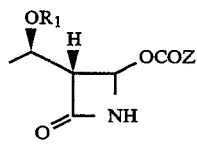

wherein $R_1$ is as defined above and Z is a $C_1$-$C_{10}$ alkyl or an aryl group, with a compound of the formula (III):

wherein $R_1$ is as defined above and M is hydrogen atom or a cation, to obtain an azetidinone of the formula IV):

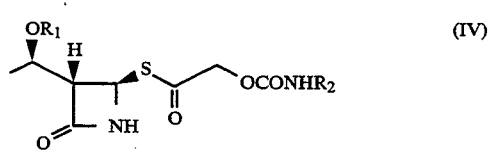

wherein $R_1$ and $R_2$ are as defined above, b) condensing the azetidinone of the formula (IV) as defined above with an acetoxymethyl oxalic acid derivative of the formula (V):

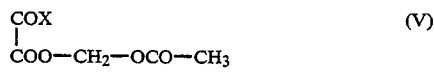

wherein X is a halogen atom or a —$OCOOR_3$ group wherein $R_3$ is a $C_1$-$C_{10}$ alkyl group,

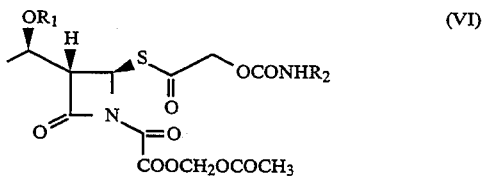

wherein $R_1$ and $R_2$ are as defined above, and c) cyclizing and optionally removing the protecting groups of the compounds of the formula (VI) as defined above.

The configuration of the compounds of the formula (I) is 5R, 6S, 1R; the configuration of the compounds of formula (IV) is 1R, 3S, 4R.

The hydroxy protecting group $R_1$ may be, for example, t-butyldimethylsilyl, p-nitrobenzyloxycarbonyl, 2,2,2-trichloroethoxycarbonyl, trimethylsilyl, benzyl, p-bromophenacyl, triphenylmethyl or pyranyl group, preferably t-butyldimethylsilyl, p-nitrobenzyloxycarbonyl, trimethylsilyl or pyranyl groups, in particular t-butyldimethylsilyl or trimethylsilyl group.

When $R_2$ is a $C_1$-$C_6$ alkyl group, it is preferably methyl or ethyl group; most preferably $R_2$ represents a hydrogen atom.

When Z is a $C_1$-$C_{10}$ alkyl, it is preferably methyl, ethyl or propyl group; when Z is an aryl group, it is preferably phenyl unsubstituted or substituted by an electron withdrawing group such as a nitro, a methoxy group, or a halogen atom, such as, e.g. bromine, chlorine or iodine. The cation M preferably represents an alkali or an alkaline-earth metal, in particular sodium or potassium, or an ammonium or an alkylammonium group.

When X is a —$OCOOR_3$ group, $R_3$ is preferably a $C_1$-$C_6$ alkyl group, in particular methyl, ethyl, propyl or butyl group.

In particular the reaction between the compounds of the formula (II) and the compounds of the formula (III) in step (a) may be carried out, e.g., in a solid-liquid phase or in a homogeneous phase, in an anhydrous organic solvent, at a temperature of from 20° to 100° C. for a period of from a few minutes to a few days, optionally operating in presence of a quaternary ammonium or phosphonium salt or of trialkylsilyl iodide.

Preferably the anhydrous organic solvents may be, e.g., toluene, xylene, methylenechloride, chloroform, diethyl-ether, dioxane, tetrahydrofurane, acetonitrile, acetone, dimethylformamide; in particular toluene, dioxane and tetrahydrofurane are the preferred ones. The reaction is preferably carried out at from, e.g., about 25° to about, e.g., 60° C. for from about, e.g., 2 hours to about, e.g., 24 hours. The quaternary ammonium or phosphonium salt may be, e.g., a cyclic or acyclic tetraalkyl, tetraaralkyl, mixed alkyl-aralkyl ammonium or phosphonium salt, or tetraalkylammonium halogenides. In particular tetraethyl or tetrabutyl ammonium chlorides or bromides are preferred. The trialkylsilyl iodide may be, e.g., trimethylsilyl or triethylsilyl iodide, and may be, if desired, prepared "in situ" from the corresponding trialkylsilyl chloride with an alkali iodide, such as KI or NaI.

The reaction between the compound of formula (V) and the compound of formula (IV) in step (b) is preferably carried out in an anhydrous organic solvent, at a temperature of from −40° C. to +40° C. in presence of an organic or inorganic base. The anhydrous organic solvent may be, e.g., toluene, xylene, methylene chloride, chloroform and diethyl ether, preferably it is e.g., toluene, xylene, diethyl ether and chloroform. The organic base may be, e.g., a cyclic or acyclic trialkylamine, a mixed alkylarylamine, an arylamine, or a mixed heteroaromatic alkyl amine; preferably it is, e.g., dimethylaminopyridine or triethylamine.

The final cyclisation of step (c) is typically operated by reacting the compound of the formula (VI) with up two mole equivalents of a trivalent organophosphorus compound in an inert solvent. The reaction generally proceeds at a temperature of from 100° to 150° C. for a period of from 2 hours to a few days. The organophosphorus compound may be a cyclic or acyclic trialkylphosphite, triarylphosphite, mixed arylphosphite or phosphoramide. Trialkylphosphites, especially triethylphosphite are preferred. Suitable inert solvents include toluene and xylene. Toluene is the preferred solvent. The reaction is preferably conducted at about 110° C. for from 5 to 15 hours.

The optional final removal of the protecting groups may be carried out by known methods, such as, for instance, hydrogenolysis, e.g. in the presence of palladium on charcoal as catalysts or by hydrolysis, either acid hydrolysis, e.g. with acetic acid or oxalic acid, or neutral hydrolysis in the presence of $SiO_2$, or basic hydrolysis, or hydrolysis under reductive conditions, for example by the use of $Fe/NH_4Cl$ or of $Na_2S_2O_4$.

The starting compounds of formula (III) and (V) are known. The azetidinones of the formula (II) are also known or may be prepared as described on the above cited patent specifications. Unless otherwise specified, an alkyl group herein is typically a $C_1$-$C_6$ alkyl group and is preferably a $C_1$-$C_4$ alkyl group. An aryl group, whether as such or as part of an aralkyl group, is typically phenyl.

Further objects of the present invention are:

(i) a process for preparing a compound of the formula (IV) as defined above by reacting a compound of the formula (II) as defined above, with a compound of the formula (III) as defined above;

(ii) a process for preparing a compound of the formula (VI) as defined above by condensing a compound of the formula (IV) as defined above, with a compound of the formula (V) as defined above; and (iii) a pharmaceutical composition comprising a pharmaceutically acceptable carrier or diluent and, as active ingredient, a compound of formula (I) which has been prepared by the present process.

The present invention also comprises a process for preparing the intermediate of the formula (V) as defined above, characterized by oxidizing the compound of the formula:

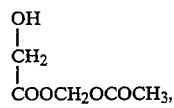

with $CrO_3$ in an aqueous acid solution, aqueous-organic solution or an organic solvent such as, e.g., acetone or acetonitrile. Surprisingly only these oxidation conditions produce satisfactory yields of the oxalic derivative.

The resultant acetoxymethyl oxalic acid of the formula:

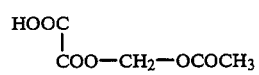

is then converted into the activated acetoxymethyl oxalic acid derivative of the formula (V). Known methods can be used. For example, the conversion may be carried out in an anhydrous organic solvent, reacting the acetoxymethyl oxalic acid with a halogenating agent such as, e.g., an oxalyl halide, preferably oxalyl chloride, or with a compound of the formula $R_3OCOY$, wherein $R_3$ is as described above and Y is a halogen atom, preferably chlorine, optionally in the presence of an organic base such as, e.g., triethylamine.

The following preparations and Examples illustrate the invention.

EXAMPLE 1

Acetoxymethyl oxalylchloride (V, X=Cl)

To a suspension of potassium glycolate (11.4 g) in acetonitrile (30 ml) KI (0.5 g) and acetoxymethyl bromide (19 g) were added. The mixture was stirred at 50° C. for 6 hours, and then cooled to room temperature. Diethyl ether was added and the solid filtered off. The solution was evaporated in vacuo and the oily residue was purified by column chromatography to yield 8 g of acetoxymethyl glycolate as a colourless oil.

NMR ($CDCl_3$) δ (ppm): 2.08 (3H, s); 2.72 (1H, s); 4.18 (2H, s); 5.76 (2H, s).

To a solution of acetoxymethyl glycolate (1.48 g) in acetone (200 ml) 10 ml of Jones reagent were added. The reaction mixture was stirred for two hours. Isopropyl alcohol was added, and the green solid filtered off. The solvent was removed in vacuo and the residue was taken up with water. Sodium chloride was added and the aqueous solution was repeatedly extracted with ethyl acetate. The collected organic layers were dried with anhydrous $Na_2SO_4$, and concentrated in vacuo to give the desired product as an amorphous solid.

Crystallization from $CHCl_3$ yielded the acetoxymethyl oxalic acid as white crystals (1.1 g, 65% yield). NMR ($CDC_3$) δ (ppm): 2.1 (3H, s); 5.81 (2H, s); 7 (1H, br. s). MS (EI,m/z): 162 (M+, 100).

To the above acid (1.62 g) in diethyl ether (100 ml) oxalyl chloride (0.96 ml) and a drop of DMF were added at 0° C. while stirring. After the gas evolution had ceased, the solvent was removed in vacuo and the oily residue was distilled (bulb to bulb distillation) to yield 1.5 g of the title product as a colourless liquid, which was characterized as its benzyl ester.

NMR ($CDCl_3$) δ (ppm): 2.1 (3H, s); 5.4 (2H, s); 5.95 (2H, s); 7.5 (5H, s).

EXAMPLE 2

4 (R)-carbamoyloxyacetylthio-3(S)-(1(R)t-butyldimethylsilyoxyethyl)azetidin-2-one (IV, $R_1$=t-butyldimethylsilyl, $R_2$=H).

Method A

To a solution of 4-acetoxy-3-(S)-(1(R)-t-butyldimethylsilyloxyethyl)-azetidin-2-one (287 mg) (II, Z=CH$_3$; $R_1$=t-butyldimethylsilyl) in anhydrous dioxane (30 ml) the sodium salt of carbamoyloxythio-acetic acid (III, M=Na, $R_2$=H) (314 mg) was added. The suspension was stirred for 20 minutes at room temperature, diethyl ether was added (30 ml), and the organic solution was washed with brine, water, dried over Na$_2$SO$_4$, and evaporated in vacuo. The oily residue was purified by column chromatography to yield 90 mg of unreacted starting material and 170 mg of the title product as a white solid (67% yield, based on reacted product).

NMR (CDCl$_3$) δ (ppm): 0.1 (6H,s); 0.75 (9H,s); 1.18 (3H, d); 3.18 (1H, dd); 4.23 (1H, m); 4.75 (2H, ABq); 5.35 (1H, d); 5.45 (2H, br.s); 7 (1H,s)

Method B

A mixture of 4-acetoxy-3(S)-(l(R)t-butyldimethylsilyloxyethyl)azetidin-2-one (287 mg), sodium salt of carbamoyloxythioacetic acid (314 mg), and tetraethylammonium chloride (20 mg) in diethyl ether was stirred at room temperature overnight yielding the title product (HPLC assay vs. standard).

Method C

The reaction was carried out as in methods A and B except that 4-benzoyloxy-3(S)-(1-(R)-t-butyldimethylsilyloxyethyl)-azetidin-2-one (350 mg) (II, $R_1$=t-butyldimethylsilyl, Z=Ph) was used as starting material yielding 200 mg of the title product.

Method D

To a solution of 4-acetoxy-3(S)-[1(R)-terbutyldimethyl-silyloxyethyl]-azetidin-2-one (287 mg) in dry acetonitrile (10 ml) trimethylsilyl chloride (0.098 ml) and KI (300 mg) were added. After 15 minutes carbamoyloxythioalacetic acid (169 mg) was added, and the resulting mixture was stirred at room temperature for 30 minutes. An excess of propylene oxide was added and after aqueous work-up and chromatographic purification the title product was obtained (78 mg, 31% yield).

EXAMPLE 3

Acetoxymethyl (5R,6S)-2-carbamoyloxymethyl-6-(1(R)-t-butyldimethylsilyloxyethyl)-penem-3-carboxylate (I, $R_1$=t-butyldimethyl-silyl, $R_2$=H).

To 0.5 g of 4(R)-carbamoyloxyacetylthio-3(S)-(1(R)-t-butyldimethylsilyloxyethyl)azetidin-2-one in 50 ml of dry toluene at 0° C., 0.25 ml of triethylamine and 0.33 ml of acetoxymethyl oxalyl chloride were added dropwise. After ten minutes stirring, the reaction mixture was diluted with diethyl ether, washed with water, brine, and dried over Na$_2$SO$_4$. Diethyl ether was removed in vacuo and to the residual toluenic solution heated to mild reflux, 0.7 ml of triethyl phosphite were added. The solution was then refluxed for 6 hours. To the cooled solution diethyl ether was added, and the solution was then washed with phosphate buffer (pH=6.5), water, dried over Na$_2$SO$_4$, and concentrated in vacuo. The crude residue was purified by column chromatography to give 0.47 g of the title product as a white solid.

NMR (CDCl$_3$) δ (ppm): 0.7 (6H, s); 0.87 (9H, s); 1.23 (3H, d); 2.11 (3H, s); 3.7 (1H, dd]; 4.22 (1H, m); 4.85 (2H, br.s); 5.05 and 5.48 (2H, ABq); 5.58 (1H, d); 5.33(2H, ABq).

We claim:

1. A process for preparing a compound of the formula (I):

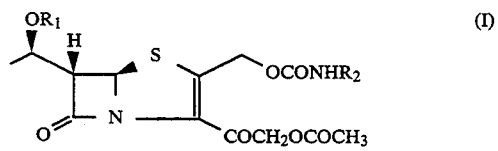

wherein $R_1$ is a hydrogen atom or a hydroxy protecting group and $R_2$ is a hydrogen atom or a $C_1$-$C_6$ alkyl group, the process comprising the following steps:

a) reacting a compound of the formula (II):

wherein $R_1$ is a hydroxy protecting group and Z is a $C_1$-$C_{10}$ alkyl or an aryl group, with a compound of the formula (III):

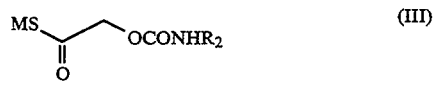

wherein $R_2$ is as defined above and M is a hydrogen atom or a cation, in the presence of an anhydrous organic solvent, at a temperature of from 20° C. to 100° C. for a period of from a few minutes to a few days, to obtain an azetidinone of the formula (IV):

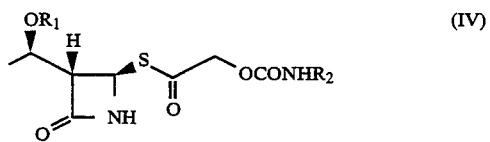

wherein $R_1$ is a hydroxy protecting group and $R_2$ is as defined above;

b) condensing the azetidinone of the formula (IV) as defined above, with an acetoxymethyl oxalic acid derivative of the formula (V):

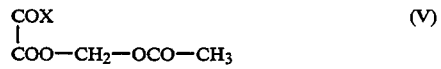

wherein X is a halogen atom or a —OCOOR$_3$ group wherein $R_3$ is a $C_1$-$C_{10}$ alkyl group, to give a compound of the formula (VI):

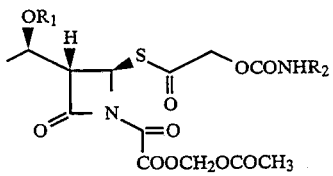

wherein $R_1$ is a hydroxy protecting group and $R_2$ is as defined above; and c) cyclizing and removing the protecting groups of the compound of the formula (VI) as defined above.

2. A process for preparing a compound of the formula (IV) as defined in claim 1, which comprises reacting a compound of the formula (II) as defined in claim 1 with a compound of the formula (III) as defined in claim 1.

3. A process according to claim 1 wherein Z is phenyl.

4. A process according to claim 1 wherein M is an alkali or an alkaline-earth metal.

5. A process according to claim 1 wherein M is hydrogen, sodium or potassium.

6. A process according to claim 1 wherein the anhydrous organic solvent used in step (a) is toluene, xylene, methylenechloride, chloroform, diethylether, dioxane, tetrahydrofurane, acetonitrile, acetone or dimethylformamide.

7. A process according to claim 1 wherein the reaction is carried out at temperature of from 25° C. to 60° C. for a period of from 2 hours to 24 hours.

8. A process according to claim 1 wherein the reaction is carried out in the presence of a quaternary ammonium or phosphonium salt or of a trialkylsilyliodide.

9. A process according to claim 8 wherein the quaternary ammonium or phosphonium salt is a cyclic or acyclic tetraalkyl, tetraaralkyl, mixed alkyl-aralkyl ammonium or phosphonium salt or a tetraalkylammonium halogenide, or wherein the trialkylsilyl iodide is trimethylsilyl iodide prepared "in situ" from trimethylsilyl chloride with potassium iodide.

10. A process for preparing a compound of formula (VI) as defined in claim 1, which comprises condensing a compound of the formula (IV) as defined in claim 1 with a compound of the formula (V) as defined in claim 1.

11. A process according to claim 1 wherein the condensation between the compound of the formula (V) and the compound of the formula (IV) is carried out in an anhydrous organic solvent, at a temperature of from −40° C. to +40° C. in presence of a base.

12. A process according to claim 11 wherein the anhydrous organic solvent is toluene, xylene, methylene chloride, chloroform or diethyl ether.

13. A process according to claim 11 wherein the base is a cyclic or acyclic trialkylamine, a mixed alkylarylamine, an arylamine, or a mixed heteroaromatic alkyl amine.

14. A process according to claim 1 wherein $R_1$ is a t-butyldimethylsilyl, p-nitrobenzyloxycarbonyl, 2,2,2-trichloroethoxycarbonyl, trimethylsilyl, benzyl, p-bromophencyl, triphenylmethyl or pyranyl group.

15. A process according to claim 1 wherein $R_2$ is hydrogen.

16. A process according to claim 1 wherein the compound of the formula (V):

wherein X is as defined in claim 1, is prepared by a process which comprises:

(a) oxidizing a compound of the formula (VII):

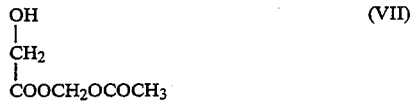

with $CrO_3$ in an aqueous acid solution, aqueous organic solution or organic solvent, to obtain a compound of the formula (VIII):

and (b) converting the compound of formula (VIII) into the compound of formula (V).

17. A process according to claim 16 wherein the organic solvent is acetone or acetonitrile.

* * * * *